(12) United States Patent
Katinger et al.

(10) Patent No.: US 7,101,664 B2
(45) Date of Patent: Sep. 5, 2006

(54) BIOACTIVE OLIGOPEPTIDES

(75) Inventors: Hermann Katinger, Vienna (AT); Frantisek Franek, Prague (CZ)

(73) Assignee: Polymun Scientific Immunbiologische Forschung GmbH, Vienna (AT)

( * ) Notice: Subject to any disclaimer, the term of this patent is extended or adjusted under 35 U.S.C. 154(b) by 380 days.

(21) Appl. No.: 10/168,690

(22) PCT Filed: Dec. 22, 2000

(86) PCT No.: PCT/EP00/13152

§ 371 (c)(1), (2), (4) Date: Sep. 26, 2002

(87) PCT Pub. No.: WO01/46220

PCT Pub. Date: Jun. 28, 2001

(65) Prior Publication Data

US 2004/0072341 A1    Apr. 15, 2004

Related U.S. Application Data

(60) Provisional application No. 60/171,497, filed on Dec. 22, 1999.

(51) Int. Cl.
*C12Q 1/68* (2006.01)
*A61K 38/00* (2006.01)
*A61K 38/28* (2006.01)

(52) U.S. Cl. .............. 435/6; 514/2; 514/17; 514/18

(58) Field of Classification Search ............ None
See application file for complete search history.

(56) References Cited

FOREIGN PATENT DOCUMENTS

| DE | 42 44 415 A | * | 6/1994 |
|---|---|---|---|
| JP | 49 035555 B | | 9/1974 |
| WO | 92 09298 A | | 6/1992 |
| WO | 99 46285 A | | 9/1999 |

OTHER PUBLICATIONS

Ito et al. 1996, Experimental Cell Research, vol. 56, pp. 10-14.*
Ito et al., Experimental Cell Research, ol. 56, No. 1, pp. 10-14 (1969).
Shimizu et al., Biochemistry International, vol. 24, No. 6, pp. 1127-1134 (1991).
Database Medline (Online), US National Library of Medicine (NLM), XP002172992 & In Vitro, vol. 17, No. 6, pp. 459-466 (1981).

* cited by examiner

*Primary Examiner*—B. Dell Chism
(74) *Attorney, Agent, or Firm*—Birch, Stewart, Kolasch & Birch, LLP

(57) ABSTRACT

The invention relates to short 3- to 10-mer bioactive oligopeptides composed of amino acid residues selected from the group consisting of glycine, alanine, β-alanine, serine, histidine, glutamic acid, aspartic acid, lysine and arginine. They are able to improve at least one cell culture parameter such as growth rate, viable cell number, viability on day 6 or 7, or final product yield, when added to the basal nutrient medium. The invention further relates to mixtures of such oligopeptides and to a method of improving cell culture parameters by incubating animal or plant cells in the presence of said oligopeptides.

8 Claims, No Drawings

SEQUENCE LISTING

```
<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 1

Gly Gly Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 2

Ala Ala Ala Ala
1

<210> SEQ ID NO 3
<211> LENGTH: 4
<212> TYPE: PRT
<213> ORGANISM: Artificial Sequence
<220> FEATURE:
```

```
<221> NAME/KEY: PEPTIDE
<222> LOCATION: (1)..(4)
<223> OTHER INFORMATION: /note: Xaa = bAla
<220> FEATURE:
<223> OTHER INFORMATION: Description of Artificial Sequence: linear
      peptide

<400> SEQUENCE: 3

Xaa Xaa Xaa Xaa
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 4

Ser Ser Ser Ser
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 5

Thr Thr Thr Thr
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 6

Ser Ser Gly Ala
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 7

Ser Gly Ser Ala
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 8
```

```
Ala His Gly Lys
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 9

Ser Gly Glu Thr
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 10

Gly Asp Ala Lys
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 11

Ala Arg Ser Thr
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 12

Glu Gly Thr His
1

<210> SEQ ID NO 13
<211> LENGTH: 4
<212> TYPE: PRT
<213> ORGANISM: Artificial Sequence
<220> FEATURE:
<221> NAME/KEY: PEPTIDE
<222> LOCATION: (1)..(3)
<223> OTHER INFORMATION: /note: Xaa = bAla
<220> FEATURE:
<223> OTHER INFORMATION: Description of Artificial Sequence: linear
      peptide

<400> SEQUENCE: 13

Xaa Xaa Xaa Ser
1

<210> SEQ ID NO 14
```

```
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 14

Gly Gly His Gly
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 15

Gly Gly Glu Ala
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: linear
      peptide

<400> SEQUENCE: 16

Gly Gly Lys Ala
1

<210> SEQ ID NO 17
<211> LENGTH: 4
<212> TYPE: PRT
<213> ORGANISM: Artificial Sequence
<220> FEATURE:
<221> NAME/KEY: PEPTIDE
<222> LOCATION: (2)
<223> OTHER INFORMATION: /note: Xaa = bAla
<220> FEATURE:
<223> OTHER INFORMATION: Description of Artificial Sequence: linear
      peptide

<400> SEQUENCE: 17

Gly Xaa Gly Gly
1

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 18

Gly Gly Gly Gly Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: linear
``` peptide

<400> SEQUENCE: 19

Ala Ala Ala Ala Ala
1               5

<210> SEQ ID NO 20
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: /note: Xaa = bAla
<220> FEATURE:
<223> OTHER INFORMATION: Description of Artificial Sequence: linear
      peptide

<400> SEQUENCE: 20

Xaa Xaa Xaa Xaa Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 21

Ser Ser Ser Ser Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 22

Thr Thr Thr Thr Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 23

Ala Ala Ala Gly Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 24

Ala Ser Ser His Thr

```
1               5

<210> SEQ ID NO 25
<211> LENGTH: 5
<212> TYPE: PRT
<213> ORGANISM: Artificial Sequence
<220> FEATURE:
<221> NAME/KEY: PEPTIDE
<222> LOCATION: (4)
<223> OTHER INFORMATION: /note: Xaa = bAla
<220> FEATURE:
<223> OTHER INFORMATION: Description of Artificial Sequence: linear
      peptide

<400> SEQUENCE: 25

Gly Ser Gly Xaa Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 26

Gly Thr Arg Ser Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 27

Ala Ala Gly Gly Lys
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: linear
      peptide

<400> SEQUENCE: 28

Glu Ala Ala Ser Ser
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: linear
      peptide

<400> SEQUENCE: 29

Gly Gly Gly Gly Gly Gly
1               5
```

BIOACTIVE OLIGOPEPTIDES

This application is the national phase under 35 U.S.C. § 371 of PCT International Application No. PCT/EP00/13152 which has an International filing date of Dec. 22, 2000, which claims the benefit of U.S. application No. 60/171,497, filed Dec. 22, 1999.

TECHNICAL FIELD

The invention relates to synthetic, short-chain oligopeptides with bioactive properties and their use for the supplementation of cell culture media.

BACKGROUND OF THE INVENTION

The biotechnological production of biologically active proteins is essential for the development of novel therapeutic and diagnostic tools and procedures. The majority of these synthetically produced peptides is at present obtained from animal cell cultures. In spite of rapidly accumulating knowledge in this field, some aspects of the in vitro production systems such as, for example, cell proliferation and cell death, are still not entirely controllable.

Industrial processes employing animal cells, particularly permanent animal cell lines, require cell numbers in the order of $10^8$ to $10^{12}$ cells. According to GMP (good manufacturing practice), the production of a new lot of product has to be started by thawing a frozen cell stock from the master cell bank. The overall efficiency of the culturing and manufacturing process largely depends on the time period necessary for the first cycles of multiplication of the cells starting from a small frozen inoculum.

Speeding up the growth of the cell population can be achieved by supplementing the culture media with nutritional supplements or growth factors. For instance, it is known in the art to use glutamine dipeptide in replacement of monomeric glutamine, because the dimeric form of glutamine is more stable under cell culture conditions. Either way, however, glutamine as a monomer and as a dipeptide serves as a nutrient and is resorbed and metabolized by the cells of the cell culture.

Growth factors may be, for instance, components of animal sera. Their main disadvantage is that they are usually not well defined. Moreover, the use of components of direct animal origin is presently discouraged in pharmaceutical industry due to the danger of transferring viruses, prions or other possibly pathogenic agents from the animal body to the desired end product, e.g., the bioactive proteins. Alternatively, recombinant growth factors, such as insulin or members of the interleukin family, may serve as suitable growth stimulants. Another possibility is to use safe, chemically defined culture media free of any protein component. However, as a rule the generation time in protein-free media is longer than in media supplemented with serum.

Therefore, there is a great demand for techniques capable to intensify and accelerate the growth and/or product yield of cultured animal cells as well as the cell viability during incubation, particularly for industrial scale manufacturing processes. The present invention will contribute to satisfying this demand.

SUMMARY OF THE INVENTION

It has been found that small oligopeptides composed of a sequence of particular amino acid residues are capable of significantly promoting the cultivation of cells by enhancing the growth rate and/or the product yield or improve at least the maintenance (i.e. viability) of animal cell lines in culture when added to basal media containing otherwise suitable nutrient mixtures. Unlike the use of nutritional supplements such as, for instance, glutamine dipeptides, the present oligopeptides are not taken up by the cells in a substantial amount, i.e. not more than up to approximately 10% of the total amount of oligopeptides supplied to a cell culture medium is taken up by the cells and possibly metabolized. Experiments have shown that although a portion of the oligopeptides present in the nutrient medium may be hydrolyzed be exogenous proteases, neither the resulting monomers nor the remaining oligomers serve as nutritional factors.

Furthermore, when operating the cell cultures in a semi-continuous mode or in a fed-batch mode, i.e. by adding the required amino acids and, optionally, the oligopeptides of the present invention in intervals over the entire cultivation period of up to 8 days, the yield of the desired protein products obtainable from these animal cell cultures is augmented in addition to the biomass concentration, as shown in subsequent Tables 9 and 10.

The upper limit for the chain length of the amino acid-sequence is primarily determined by the solubility of the respective peptides in the desired aqueous cell culture media. Usually, the chain length does not exceed six amino acid residues, because peptides longer than six amino acid residues cannot normally be dissolved at a concentration sufficiently high for effectively causing growth stimulation with the treated cells. In most cases, a chain length of three to five amino acid residues may be sufficient to produce the bioactive, e.g. growth stimulating, effects described herein.

The stimulatory effects on the cell cultures shows a tendency to increase with the oligopeptide concentration in the medium. In a preferred embodiment of the invention, oligopeptides or mixtures thereof are provided in a concentration range of 0.01 to 2.5 percent (w/v), i.e., 0.1 to 25 g/l, in particular from about 0.05 to 2% (w/v) corresponding to 0.5 to 20 g/l, in the cell culture nutrient medium, to effectively intensify the growth and/or product yield and the viability of the cultured cells.

The composition of the basal medium is not critical to the stimulatory effect of the present oligopeptides. Any suitable nutrient medium applicable in the cultivation of a desired animal cell line may be used. Also, the cell stimulating properties of the present oligopeptides are not restricted to any specific cell lines but apply to a multitude of different kinds of eukaryotic cells including plant and animal cells.

DETAILED DESCRIPTION OF THE INVENTION

The terms "peptides" or "oligopeptides" as used herein relate to short peptides or amino acid sequences, preferably of synthetic origin, that consist of at least two amino acid residues, preferably L-a-amino acid residues, and that do not contain more than 10, preferably not more than six, amino acid residues.

It is to be understood that "incubation" or "cultivation" of cells is carried out ex vivo under conditions favoring cell growth and continued viability.

The term "bioactive" as used herein with regard to the activity of the present oligopeptides is meant to comprise at least one of the following activities: cell growth stimulation, improvement of cell or cell culture viability (particularly at a time of incubation where cell viability starts to decline), increase of viable cell count, augmentation of product yield (e.g. of substances secreted by the cells, such as pharmaceutically active substances, drugs or antibodies), wherein this "bioactivity" of the oligopeptides is not due to a nutritional contribution of the oligopeptides. Indeed, the "bioactivity" of the present oligonucleotides is caused by effects other than a mere nutritional supplement or a compensation of nutritional deficiencies in a cell culture medium and has clearly been proven for complete nutrient media that are suitable for culturing a desired animal cell line in the absence of said oligopeptides.

The oligopeptides according to the present invention are preferably composed of amino acid residues derived from amino acids selected from the group consisting of glycine, alanine, β-alanine, serine, histidine, glutamic acid, aspartic acid, lysine and arginine. When added to a basal nutrient medium the oligopeptides are able to enhance at least one of the following cell culture parameters: number of viable cells, cell viability on day 6 or 7, viable cell count or the final product yield (e.g. a recombinant protein or an antibody). While the qualitative composition of the bioactive oligopeptides seems to be decisive for their stimulatory activity, it appears that the order of amino acids within the peptide chain may have less or no significance with regard to the extent of said activity.

Therefore, in one embodiment of the present invention the oligopeptide consists of two or more identical amino acid residues, preferably selected from the group consisting of glycine, alanine, β-alanine and serine.

In another embodiment, the oligopeptide comprises at least two, optionally three or more, identical amino acid residues selected from the group consisting of glycine, alanine, β-alanine and serine, threonine and, additionally, at least one amino acid residue selected from the group consisting of histidine, glutamic acid, aspartic acid, lysine and arginine.

The identical amino acid residues may be linked to each other either in a tandem arrangement or alternating with other residues within the oligopeptide.

Oligopeptides which contain at least one amino acid residue of alanine and/or glycine, optionally in combination with at least one further amino acid residue, have found to be particularly useful for the cultivation of cells when added to the basal medium.

Examples of bioactive tripeptides used in the present invention include but are not limited to: Gly-Gly-Gly, Ser-Ser-Ser, Ala-Ala-Ala, βAla-βAla-βAla, Thr-Thr-Thr, Glu-Gly-Gly, Glu-Gly-Ala, Ala-Asp-Ala, Ala-His-Gly, Thr-Ala-Ser, Ser-Gly-Ala, Ala-Ala-Arg, βAta-Gly-Gly, Gly-Asp-Gly, Gly-His-Gly, Gly-Lys-Gly and Gly-Arg-Gly.

Examples of bioactive tetrapeptides used in the present invention include but are not limited to: Gly-Gly-Gly-Gly (SEQ ID NO:1), Ala-Ala-Ala-Ala (SEQ ID NO:2), βAla-βAla-βAla-βAla (SEQ ID NO:3), Ser-Ser-Ser-Ser (SEQ ID NO:4), Thr-Thr-Thr-Thr (SEQ ID NO:5), Ser-Ser-Gly-Ala (SEQ ID NO:6), Ser-Gly-Ser-Ala (SEQ ID NO:7), Ala-His-Gly-Lys (SEQ ID NO:8), Ser-Gly-Glu-Thr (SEQ ID NO:9), Gly-Asp-Ala-Lys (SEQ ID NO:10), Ala-Arg-Ser-Thr (SEQ ID NO:11), Glu-Gly-Thr-His (SEQ ID NO:12), βAla-βAla-βAla-Ser (SEQ ID NO:13), Gly-Gly-His-Gly (SEQ ID NO:14), Gly-Gly-Glu-Ala (SEQ ID NO:15), Gly-Gly-Lys-Ala (SEQ ID NO:16) and Gly-βAla-Gly-Gly (SEQ ID NO:17).

Examples of the pentapeptide used in the invention include but are not limited to: Gly-Gly-Gly-Gly-Gly (SEQ ID NO:18), Ala-Ala-Ala-Ala-Ala (SEQ ID NO:19), βAla-βAla-βAla-βAla-βAla (SEQ ID NO:20), Ser-Ser-Ser-Ser-Ser (SEQ ID NO:21), Thr-Thr-Thr-Thr-Thr (SEQ ID NO:22), Ala-Ala-Ala-Gly-Ser (SEQ ID NO:23), Ala-Ser-Ser-His-Thr (SEQ ID NO:24), Gly-Ser-Gly-βAla-Gly (SEQ ID NO:25), Gly-Thr-Arg-Ser-Ser (SEQ ID NO:26), Ala-Ala-Gly-Gly-Lys (SEQ ID NO:27) and Glu-Ala-Ala-Ser-Ser (SEQ ID NO:28).

An example of the hexapeptide used in the invention include but are not limited to: Gly-Gly-Gly-Gly-Gly-Gly (SEQ ID NO :29).

The bioactive properties of the present oligonucleotides also apply to plant cell cultures in a way very similar to the ones described herein for animal cells. Preliminary experiments (data not shown herein) have confirmed the beneficial utility of the oligopeptides for different plant cell cultures.

In order that the invention described herein may be more fully understood, the following examples are set forth. The examples are for illustrative purposes only and are not to be construed as limiting this invention in any respect.

EXAMPLE 1

Comparison of Changes in Amino Acid Concentration During the Cultivation Period of an Animal Cell Culture Cells: Mouse hybridoma CAU 96 producing monoclonal lgG2a antibody. (Mouse hybridoma CAU 96 is a subclone, obtained through systemic adaptation to protein-free culture medium of hybridoma ME-750 (Franek F, Sramkova K (1998): in New Developments and New Applications in Animal Cell Culture Technology, pp 55–57, Dordrecht). The original hybridoma was constructed using the Sp2/O-Ag14 myeloma parent. This hybridoma produces an lgG2a monoclonal antibody reactive with an unidentified membrane antigen of pig lymphozytes. Hybridoma CAU 96 is deposited in the Institute of Experimaental Botany, Acadamy of Sciences of the Czech Republic, Prague.

Medium: DMEM/F-12/RPMI 1640 (2:1:1) supplemented with Basal Medium Eagle (BME) amino acids, 2.0 mM glutamine, 15 mM HEPES (N-2-Hydroxyethylpiperazine-N'-2-ethanesulfonic acid), 2.0 g/l sodium bicarbonate and 0.4 mM ferric citrate. (All medium components were obtained from Life Technologies)

Culture mode: 25 cm$^3$ T-flasks (Nunc) culture volume 6.0 ml, placed at 37° C. in an incubator with 5% $CO^2$; starting viable cell density is $3.1 \times 10^5$ cells per ml.

Preparation of samples of amino acid analysis: Cells are removed by low-speed centrifugation and macromolecular components are removed by ultrafiltration.

TABLE 1

| Amino acid or | Amino acid concentration, [mM] | | |
|---|---|---|---|
| peptide | Day 0 | Day 4 | Difference |
| Lys | 0.43 | 0.28 | −0.15 |
| His | 0.18 | 0.14 | −0.04 |
| Arg | 0.48 | 0.34 | −0.14 |
| Asp | 0.06 | 0.02 | −0.04 |
| Thr + Asn | 0.43 | 0.42 | −0.01 |
| Ser + Gln | 2.94 | 0.91 | −2.03 |
| Glu | 0.08 | 0.02 | −0.06 |
| Pro | 0.37 | 0.49 | +0.12 |
| Gly | 0.59 | 1.52 | +0.93 |
| Ala | 0.73 | 2.02 | +1.29 |
| Val | 0.72 | 0.56 | −0.16 |
| Met | 0.24 | 0.17 | −0.07 |
| Ile | 0.34 | 0.05 | −0.29 |

TABLE 1-continued

| Amino acid or peptide | Amino acid concentration, [mM] | | |
|---|---|---|---|
| | Day 0 | Day 4 | Difference |
| Leu | 0.08 | 0.04 | −0.04 |
| Tyr | 0.45 | 0.41 | −0.04 |
| Phe | 0.33 | 0.28 | −0.05 |
| Trp | 0.05 | 0 | −0.05 |
| Tetraglycine | 7.14 | 6.55 | −0.59 |
| Tetraglycine + Gly | 7.73 | 8.06 | +0.33 |

It appears, that the tetrameric glycine and alanine peptides are neither utilized nor metabolized by the cells as substrates for the synthesis of new cell mass, as shown in Table 1. The decrease of the oligoglycine, i.e. tetraglycine, concentration during the cultivation period is less than 10% (Table 1, penultimate line). Interestingly, the analytical data in Table 1 and Table 2 further suggest that the hydrolized fraction of tetraglycine or tetraalanine (probably hydrolyzed by peptidases released from the cells) is not consumed as a substrate. In the case of tetraglycine, the total glycine concentration, as well as the total sum of glycine and tetraglycine concentration (Table 1, ultimate line), is even higher after 4 days of culture than at the beginning. In the case of tetraalanine the total alanine concentration, as well as the sum of alanine and tetraalanine concentration increases during the cultivation period (Table 2, ultimate line). The decrease of tetraalanine concentration during the cultivation period corresponds to the increase of alanine concentration, most likely caused by hydrolysis of tetraalanine by peptidases released from the cells.

TABLE 2

| Amino acid or peptide | Amino acid concentration | | |
|---|---|---|---|
| | Day 0 | Day 4 | Difference |
| Lys | 0.47 | 0.36 | −0.11 |
| His | 0.18 | 0.12 | −0.06 |
| Arg | 0.45 | 0.36 | −0.09 |
| Asp | 0.10 | 0.05 | −0.05 |
| Thr + Asn | 0.47 | 0.42 | −0.05 |
| Ser + Gln | 2.38 | 0.85 | −1.53 |
| Glu | 0.08 | 0.01 | −0.07 |
| Pro | 0.39 | 0.43 | +0.04 |
| Gly | 1.00 | 0.88 | −0.12 |
| Ala | 0.48 | 2.68 | +2.20 |
| Val | 0.47 | 0.35 | −0.12 |
| Met | 0.18 | 0.11 | −0.07 |
| Ile | 0.54 | 0.22 | −0.32 |
| Leu | 0.55 | 0.22 | −0.33 |
| Tyr | 0.25 | 0.11 | −0.14 |
| Phe | 0.25 | 0.21 | −0.04 |
| Trp | 0.05 | 0.01 | −0.04 |
| Tetraalanine | 1.84 | 1.28 | −0.56 |
| Tetraalanine + Ala | 2.32 | 3.86 | +1.54 |

EXAMPLE 2

Effect of Varying Chain Length and Concentrations of Oligopeptides

Cells: Mouse hybridoma CAU 96 producing monoclonal lgG2a

Medium: DMEM/F-12/RPMI 1640 (2:1:1) supplemented with BME amino acids, MEM non essential amino acids, 2.0 mM glutamine, 15 mM HEPES, 2.0 g/L sodium bicarbonate and 0.4 mM ferric citrate.

Culture mode: 25 cm² T-flasks (Supplier: Nunc) with a culture volume of 6.0 ml, placed at 37° C. in an incubator with 5% $CO_2$ Starting viable cell density is 310000 ($3.1*10^5$) cells per ml.

TABLE 3

Effect of oligoglycines

| | Day 7 | | |
|---|---|---|---|
| Supplement (% in w/v) | Viable cell number | Viability | Monoclonal antibody |
| | cells/μL  % of control | % | mg/L |
| None (Control) | 1060    100 | 61 | 150 |
| Glycine 0.2% | 1080    102 | 60 | 160 |
| Diglycine 0.2% | 1210    114 | 70 | 165 |
| Triglycine 0.2% | 1660    157 | 75 | 160 |
| Tetraglycine 0.2% | 1870    176 | 80 | 170 |
| Pentaglycine 0.2% | 2020    190 | 82 | 165 |
| Hexaglycine 0.2% | 1940    183 | 79 | 160 |

Table 3 illustrates the effect of glycine oligopeptides of different chain length on the growth of the hybridoma cell line: the growth stimulating effect increases from diglycine to pentaglycine. The oligoglycine peptides act selectively on cell growth increasing both viable cell number and viability of the cells. The intensification of growth does not, however, automatically entail an increase in the yield of the desired protein product, e.g., an antibody.

TABLE 4

Effect of oligoalanines

| | Day 6 | | |
|---|---|---|---|
| Supplement (% in w/v) | Viable cell number | Viability | Monoclonal antibody |
| | cells/μL  % of control | % | mg/L |
| none (control) | 1100    100 | 57 | 104 |
| Alanine 0.2% | 1030     94 | 60 | 110 |
| Trialanine 0.2% | 1420    129 | 70 | 132 |
| Trialanine 0.1% | 1390    126 | 69 | 130 |
| Tetraalanine 0.2% | 1560    142 | 72 | 153 |
| Tetraalanine 0.1% | 1370    125 | 66 | 133 |

Table 4 illustrates the effect of alanine and two oligoalanines differing in chain length on the growth of the hybridoma cell line. While the growth stimulating effect of alanine is insignificant, the stimulatory effect of oligoalanines is quite pronounced and increases from trialanine to tetraalanine. Both oligoalanines display higher growth-stimulating effect at 0.2% concentration than at 0.1% concentration. In the case of oligoalanines the intensification of growth is accompanied by an increase of the yield of the desired cell product, e.g. the monoclonal antibody.

TABLE 5

Concentration-dependent effect of triserine, trithreonine and tri-β alanine

| | Day 6 | | | |
|---|---|---|---|---|
| | Viable cell number | | Viability | Monoclonal antibody |
| Supplement (% in w/v) | cells/μL | % of control | % | mg/L |
| None (control) | 1140 | 100 | 61 | 109 |
| Serine 0.2% | 1190 | 104 | 63 | 111 |
| Triserine 0.3% | 1610 | 141 | 78 | 142 |
| Triserine 0.2% | 1550 | 136 | 70 | 126 |
| Triserine 0.1% | 1340 | 118 | 65 | 112 |
| Triserine 0.05% | 1200 | 105 | 61 | 109 |
| Threonine 0.2% | 1100 | 97 | 59 | 114 |
| Trithreonine 0.2% | 1450 | 127 | 73 | 152 |
| Trithreonine 0.1% | 1370 | 120 | 70 | 130 |
| Trithreonine 0.05% | 1310 | 115 | 67 | 122 |
| β-alanine 0.2% | 1210 | 106 | 60 | 105 |
| Tri-β-alanine 0.2% | 1410 | 124 | 70 | 122 |
| Tri-β-alanine 0.1% | 1470 | 129 | 70 | 122 |
| Tri-β-alanine 0.05% | 1390 | 122 | 73 | 126 |
| Tri-β-alanine 0.02% | 1370 | 120 | 63 | 120 |
| Tri-β-alanine 0.01% | 1210 | 106 | 64 | 117 |

Table 5 illustrates that tripeptides composed of serine, threonine, or β-alanine are able to stimulate cell growth, while the effect of serine or β-alanine is insignificant. The effect of triserine and trithreonine on cell growth and antibody yield is highest at the highest peptide concentration tested, and decreases with concentration. Tri-β-alanine displays stimulating effect on cell growth and antibody yield at lower concentrations 0.1% (w/v) and 0.05% (w/v).

TABLE 6

Effect of tripeptides consisting of two glycine residues and a residue of another amino acid

| | Day 6 | | | |
|---|---|---|---|---|
| Supplement (% in w/v) | Viable cell number | | Viability | Monoclonal antibody |
| | cells/μL | % of control | % | mg/L |
| None (control) | 1250 | 100 | 55 | 88 |
| Gly-Gly-Gly 0.2% | 1300 | 104 | 80 | 89 |
| Gly-Gly-Gly 0.1% | 1350 | 108 | 78 | 98 |
| Gly-Asp-Gly 0.2% | 1420 | 114 | 70 | 92 |
| Gly-Asp-Gly 0.1% | 1340 | 107 | 64 | 98 |
| Gly-His-Gly 0.2% | 900 | 72 | 66 | 144 |
| Gly-His-Gly 0.1% | 1180 | 94 | 65 | 121 |
| Gly-Lys-Gly 0.2% | 1100 | 88 | 62 | 154 |
| Gly-Lys-Gly 0.1% | 1250 | 100 | 67 | 128 |
| Gly-Arg-Gly 0.2% | 1270 | 102 | 66 | 121 |
| Gly-Arg-Gly 0.1% | 1360 | 109 | 65 | 106 |

Table 6 illustrates the effects of several tripeptides composed of glycine residues and residues of glutamic acid, aspartic acid, histidine, lysine or arginine. None of these peptides stimulates the cell growth in a significant manner. Higher concentrations (e.g. 0.2%) of peptides containing histidine or lysine suppress the growth of hybridoma cells. A common property of peptides containing histidine, lysine or arginine is a significant enhancement of antibody yield. All tripeptides tested improve the viability of the culture on day 6, i.e. at a time where viability of the cell culture starts to decline. The results demonstrate a 64 to 80% viability in the presence of the oligopeptides, compared to only 55% viability in the control without oligopeptides)

TABLE 7

Effect of various tetrapeptides consisting of glycine, alanine, histidine, glutamic acid, lysine and β-alanine residues.

| | Day 6 | | | |
|---|---|---|---|---|
| | Viable cell number | | Viability | Monoclonal antibody |
| Supplement (% in w/v) | cells/μL | % of control | % | mg/L |
| None (control) | 1070 | 100 | 53 | 93 |
| Gly-Gly-His-Gly 0.2% | 1180 | 110 | 71 | 84 |
| Gly-Gly-His-Gly 0.1% | 1360 | 127 | 77 | 93 |
| Gly-Gly-Glu-Ala 0.2% | 1280 | 120 | 77 | 113 |
| Gly-Gly-Glu-Ala 0.1% | 1350 | 126 | 82 | 100 |
| Gly-Gly-Lys-Ala 0.2% | 1290 | 121 | 78 | 134 |
| Gly-Gly-Lys-Ala 0.1% | 1310 | 122 | 79 | 118 |
| Gly-βAla-Gly-Gly 0.2% | 1270 | 119 | 72 | 150 |
| Gly-βAla-Gly-Gly 0.1% | 1150 | 107 | 65 | 129 |
| Gly-βAla-Gly-Gly 0.05% | 1100 | 103 | 68 | 121 |

Table 7 illustrates that tetrapeptides consisting of glycine, β-alanine, glutamic acid, histidine and lysine are able to stimulate cell growth, at least at a concentration of 0.1 or 0.2%. While the enhancement of antibody yield due to the presence of the peptide containing histidine is insignificant, all other peptides increase the antibody yields. All tetrapeptides tested improve the culture viability on day 6 (65 to 82% viability with peptides versus 53% in the control without peptides)

EXAMPLE 3

Dependence of the Effect of Oligoglycine Peptides on the Concentrations Applied

Cells: Mouse hybridoma CAU 96 producing monoclonal lgG2a

Medium: DMEM/F-12/RPMI 1640 (2:1:1) supplemented with BME amino acids, MEM non essential amino acids, 2.0 mM glutamine, 15 mM HEPES, 2.0 g/L sodium bicarbonate and 0.4 mM ferric citrate.

Culture mode: 25 cm$^2$ T-flasks (Supplier: Nunc), culture volume 6.0 ml, placed at 37° C. in an incubator with 5% $CO_2$; starting viable cell density is $3.1 \times 10^5$ cells per ml.

TABLE 8

| Tetraglycine concentration | Day 7 | | | |
|---|---|---|---|---|
| | Viable cell number | | Viability | Monoclonal antibody |
| % (w/v) | cells/μL | % of control | % | mg/L |
| 0 | 1140 | 100 | 64 | 140 |
| 0.1 | 1750 | 154 | 78 | 125 |
| 0.2 | 2220 | 195 | 77 | 120 |
| 0.3 | 2370 | 208 | 80 | 110 |

From Table 3 it is derivable that glycine monomer does not significantly stimulate cell growth, while from dimeric to pentameric glycine an increasingly stimulating effect is noted. Table 8 illustrates for tetraglycine how the concentration of oligopetides in the cell culture medium affects cell growth. Indeed, cell density and viability is improved already at a tetraglycine concentration as low as 0.1%. On the other hand, the monoclonal antibody yield slightly decreases with increasing tetraglycine concentration and increasing viable cell number. This effect may possibly be similar to a certain extent to the well known distinction between growth phase and metabolite production and/or excretion phase in many conventional microbiological fermentation processes.

EXAMPLE 4

Steady State in Semi-continuous Culture in the Presence of Tetraglycine

Cells: Mouse hybridoma CAU 96 producing monoclonal lgG2a

Medium: DMEM/F-12/RPMI 1640 (2:1:1) supplemented with BME amino acids, MEM non essential amino acids, 2.0 mM glutamine, 15 mM HEPES, 2.0 g/L sodium bicarbonate and 0.4 mM ferric citrate.

Culture mode: Semicontinuous culture in 25 cm² T-flasks, total volume 6 ml, placed at 37° C. in an incubator with 5% $CO_2$; starting viable cell density is $3.1 \times 10^5$ cells per ml. A volume of 2.0 ml culture is withdrawn every day and replaced by 2.0 ml fresh medium (including the oligopeptides for the experimental cell culture, but without olipeptides for the control culture).

In semi-continuous culture both the viable cell density and viability, as well as the monoclonal antibody concentration are positively influenced by tetraglycine (see Table 9).

TABLE 9

| Medium | Viable cell number cells/μL | Viability % | Monoclonal Antibody mg/L |
|---|---|---|---|
| | Mean ± S.D. | | |
| Standard medium (control) | 1740 ± 80 | 83 ± 2 | 43 ± 6 |
| Standard medium + 0.2% tetraglycine | 2240 ± 20 | 91 ± 2 | 52 ± 8 |

EXAMPLE 5

Comparison of Batch and Fed Batch Mode Culture

Cells: Mouse hybridoma CAU 96 producing monoclonal lgG2a.

Medium: DMEM/F-12/RPMI 1640 (2:1:1) supplemented with BME amino acids, MEM non essential amino acids, 2.0 mM glutamine, 15 mM HEPES, 2.0 g/L sodium bicarbonate and 0.4 mM ferric citrate.

Culture mode: 25 cm² T-flasks (Nunc), culture volume 6.0 ml, placed at 37° C. in an incubator with 5% $CO_2$; starting viable cell density is $3.1 \times 10^5$ cells per ml.

Batch: without feeding.

Fed batch: 0.2 ml concentrated BME amino acid solution added daily from day 1.

TABLE 10

| | Standard medium (control) | | | Medium + 0.2% (w/v) tetraglycine | | |
|---|---|---|---|---|---|---|
| | Viable cell | | Monoci. | Viable cell number | | Monoci. |
| Day | number cells/μL | Viability % | antibody mg/L | cells/μL | % of control | Viability % | antibody mg/L |
| | | | BATCH | | | |
| 0 | 280 | 88 | 9 | 280 | 100 | 89 | 9 |
| 4 | 1640 | 89 | n.d. | 2070 | 138 | 89 | n.d. |
| 8 | 990 | 49 | 71 | 1660 | 168 | 58 | 69 |
| | | | FED BATCH | | | |
| 0 | 280 | 88 | 9 | 280 | 100 | 88 | 9 |
| 4 | 1850 | 90 | n.d. | 2940 | 159 | 81 | n.d. |
| 8 | 1720 | 60 | 143 | 2150 | 125 | 49 | 189 |

Feeding a concentrated amino acid solution to the starting medium results in a significant increase in the yield of the final product, e.g., the monoclonal antibodies. While in simple batch mode culture the addition of tetraglycine does not influence the final product yield, in the fed batch culture the positive effects of feeding and intensified cell growth resulted in an additive enhancement of the final product yield.

EXAMPLE 6

Effect of Tetraglycine on the Growth of CHO Cells

Cells: CHO dhf

Basal medium: DMEM/F12 supplemented with BME amino acid mixture and

MEM non-essential amino acid mixture, 0.5 mM ferric citrate

Culture mode: Batch culture in 25 cm² T-flasks (Nunc), culture volume 6.0 ml, placed at 37° C. in an incubator with 5% $CO_2$.

Starting viable cell density: 180000 cells per ml

TABLE 11

| | Viable cell number, day 6 | |
|---|---|---|
| Supplement | cells per μL | % of control |
| None (control) | 440 | 100 |
| Tetraglycine, 1.25% | 530 | 120 |
| Tetraglycine, 2.5% | 810 | 184 |

Tetraglycine also significantly affects the growth of CHO cells, suggesting that it may have a non-species specific growth stimulating effect on a variety of animal cells.

EXAMPLE 7

Combination of Various Tetrapeptides

Cells: Mouse hybridoma CAU 96 producing monoclonal lgG2a antibody

Medium: DMEM/F-12/RPMI 1640 (2:1:1) supplemented with BME amino acids, MEM non essential amino acids, 2.0 mM glutamine, 15 mM HEPES, 2.0 g/L sodium bicarbonate and 0.4 mM ferric citrate.

Culture mode: 25 cm$^2$ T-flasks (Nunc) with a culture volume of 6.0 ml, placed at 37° C. in an incubator with 5% $CO_2$.

Starting viable cell density is 310000 (3.1*10$^5$) cells per ml

TABLE 12

| | Day 6 | | |
|---|---|---|---|
| | Viable cell number | | Monoclonal |
| Supplement (% in w/v) | cells/μL | % of control | Viability % | antibody mg/L |
| None (control) | 1100 | 100 | 58 | 96 |
| Gly-Gly-His-Gly 0.1 %+ Gly-Gly-Glu-Ala 0.1 % | 1570 | 143 | 67 | 68 |

TABLE 12-continued

| | Day 6 | | |
|---|---|---|---|
| | Viable cell number | | Monoclonal |
| Supplement (% in w/v) | cells/μL | % of control | Viability % | antibody mg/L |
| Gly-Gly-His-Gly 0.1% + Gly-βAla-Gly-Gly 0.1% | 1650 | 150 | 71 | 98 |
| Gly-Gly-His-Gly 0.1% + Gly-Gly-Lys-Ala 0.1% | 1420 | 129 | 73 | 110 |
| Gly-Gly-Glu-Ala 0.1% + Gly-Gly-Lys-Ala 0.1 | 1200 | 109 | 69 | 94 |
| Gly-Gly-Lys-Ala 0.1% + Gly-βAla-Gly-Gly 0.1% | 1470 | 134 | 77 | 111 |
| Gly-Gly-Glu-Ala 0.1% + Gly-βAla-Gly-Gly 0.1% | 1430 | 130 | 69 | 74 |

Table 12 demonstrates that tetrapeptides comprising amino acid residues selected from the group consisting of glycine, alanine, histidine, glutamic acid, lysine and β-alanine residues stimulate cell growth when added as a combination of two different peptides. The growth promoting activity of the oligopeptide pairs does not likewise extend, however, to the product, i.e. antibody yield. On the contrary, the product yield is lower than in case of application of the corresponding single tetrapeptides, as referred to in Table 7. All of the peptide pairs retain their ability of improving the culture viability on day 6.

What is claimed is:

1. A method of increasing the yield of a desired cell product in an animal or plant cell culture, as compared to a control culture, said method comprising:
   preparing a nutrient medium suitable for animal or plant cell culture that contains a bioactive oligipeptide selected from the group consisting of Gly-Lys-Gly, Gly-His-Gly, Gly-Arg-Gly and mixtures thereof; and
   culturing animal or plant cells in said nutrient medium.

2. A method of increasing the yield of a desired cell product in an animal or plant cell culture, as compared to a control cell culture, said method comprising:
   preparing a nutrient medium suitable for animal or plant cell culture containing a bioactive
      oligoeptide selected from the group consisting of Ser-Ser-Ser, Ala-Ala-Ala, β-Ala-β-Ala-β-Ala, Thr-Thr-Thr, Gly-His-Gly, Gly-Lys-Gly, Gly-Arg-Gly, Ala-Ala-Ala-Ala (SEQ ID NO:2), β-Ala-β-Ala-β-Ala-βAla (SEQ ID NO:3), Gly-Gly-Glu-Ala (SEQ ID NO:15), Gly-Gly-Lys-Ala (SEQ ID NO: 16), Gly-β-Ala-Gly-Gly (SEQ ID NO: 17), Gly-Gly-Gly-Gly-Gly- (SEQ ID NO: 18), Ala-Ala-Ala-Ala-Ala (SEQ ID NO: 19), β-Ala-β-Ala-β-Ala-β-Ala-β-Ala (SEQ ID NO:20), Gly-Gly-Gly-Gly-Gly-Gly (SEQ ID NO:29), and mixtures thereof; and
   incubating animal or plant cells in said nutrient medium.

3. The method according to claim 1, wherein the bioactive oligopeptides are present in the nutrient medium at a concentration of 0.01 to 2.5 percent (w/v), corresponding to 0.1 to 25 g per liter nutrient medium.

4. The method according to claim 1, wherein the desired cell product is a pharmaceutically active substance.

5. The method according to claim 2, wherein the bioactive oligopeptide is present in the nutrient medium at a concentration of 0.01 to 2.5 percent (w/v), corresponding to 0.1 to 25 g per liter nutrient medium.

6. The method according to claim 4, wherein the desired cell product is a drug or an antibody.

7. The method according to claim 1, wherein said bioactive oligopeptide is Gly-Lys-Gly.

8. The method according to claim 1, wherein said nutrient medium is a basal nutrient medium.

* * * * *